United States Patent [19]

Broger et al.

[11] Patent Number: 4,652,657
[45] Date of Patent: Mar. 24, 1987

[54] CHIRAL RHODIUM-DIPHOSPHINE COMPLEXES

[75] Inventors: Emil A. Broger, Magden; Yvo Crameri, Oberwil, both of Switzerland

[73] Assignee: Hoffmann-La Roche Inc., Nutley, N.J.

[21] Appl. No.: 721,826

[22] Filed: Apr. 10, 1985

[30] Foreign Application Priority Data

Apr. 19, 1984 [CH] Switzerland ........................ 1967/84
Feb. 7, 1985 [CH] Switzerland ........................ 547/85

[51] Int. Cl.$^4$ .............................................. C07F 15/00
[52] U.S. Cl. .................................... 548/402; 549/319; 560/179; 562/446
[58] Field of Search ................... 548/402, 412; 556/21; 656/20

[56] References Cited

U.S. PATENT DOCUMENTS 3,739,003  6/1973  Codet et al. ................... 556/21 X
3,794,671  2/1974  Wilkinson .................... 556/21 X
4,343,741  8/1982  Townsend et al. ............. 548/412
4,539,411  9/1985  Broger et al. ................. 548/402

FOREIGN PATENT DOCUMENTS 3302697  8/1983  Fed. Rep. of Germany .
1368431  9/1974  United Kingdom .
2114134  8/1983  United Kingdom .

OTHER PUBLICATIONS

Uson, et al., Chem. Abs., 86:190183H, (1977).
Vastag et al., J. Molecular Catalysts, 1984, 22:283-287.
Mitchell et al., J. Chem. Soc. (A), 1971, 3224-3230.
Knowles et al., "Catalytic Aspects of Metal Phosphine Complexes", Advances in Chemistry Series, 196, 1982, Studies of Asymmetric Homogenous Catalysts, pp. 325–336, (1982).
Brunner, Chemie in Unserer Zeit, vol. 14, No. 6, pp. 177-183, (1980).
Patent Abstracts of Japan, C-60, 5, No. 9, Jun. 25, 1981.

Primary Examiner—Donald G. Daus
Assistant Examiner—Diana G. Rivers
Attorney, Agent, or Firm—Jon S. Saxe; George M. Gould; Julie M. Prlina

[57] ABSTRACT

There are described novel chiral rhodium-diphosphine complexes of the formula

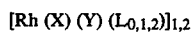

$$[Rh(X)(Y)(L_{0,1,2})]_{1,2} \qquad I$$

wherein X, which may be fixed to a carrier, is Z—COO$^-$, wherein Z is

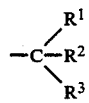

perfluorophenyl, perfluorobiphenyl or a residue of the formula

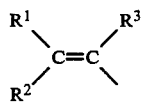

and R$^1$, R$^2$ and R$^3$ is halogen, lower alkyl, perfluorophenyl, perfluoro-C$_{1-20}$-alkyl, hydrogen or the group —COA or AOC—(CF$_2$)$_n$— in which A is —OR or —NR'$_2$, except that at least one of the substituents R$^1$, R$^2$ and R$^3$ is fluorine, R is hydrogen, lower alkyl or a cation, R' is hydrogen or lower alkyl and n is 1 to 20 and wherein Y is a chiral diphosphine ligand and L is a neutral ligand.

16 Claims, No Drawings

CHIRAL RHODIUM-DIPHOSPHINE COMPLEXES

The present invention relates to novel chiral rhodium-diphosphine complexes of the formula $$[Rh(X)(Y)(L_{0,1,2})]_{1,2} \qquad \text{I}$$

wherein X, which may be fixed to a carrier, is Z—COO$^-$, wherein Z is

perfluorophenyl, perfluorobiphenyl or a residue of the formula

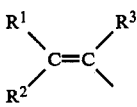

and $R^1$, $R^2$ and $R^3$ is halogen, lower alkyl, perfluorophenyl, perfluoro-$C_{1-20}$-alkyl, hydrogen or the group —COA or AOC—$(CF_2)_n$— in which A is —OR or —NR'$_2$, except that at least one of the substituents $R^1$, $R^2$ and $R^3$ is fluorine, R is hydrogen, lower alkyl or a cation, R' is hydrogen or lower alkyl and n is 1 to 20 and wherein Y is a chiral diphosphine ligand and L is a neutral ligand.

The invention is also concerned with the manufacture of the rhodium-diphosphine complexes of formula I, as well as their use for asymmetric hydrogenations.

Chiral rhodium-diphosphine complexes and their use in asymmetric hydrogenations are known in the literature. Usually these complexes are cationic or contain—when they are neutral—chlorine, bromine or iodine as the ligand X. The optical yields obtained with the use of such complexes is asymmetric hydrogenations typically in the most favourable cases are approximately 80–84% in the case of the hydrogenation of ketopantolactone.

DETAILED DESCRIPTION

It has now been found that the rhodium-diphosphine complexes of formula I in accordance with the invention are considerably more active and enantioselective than previously known complexes. The rhodium-diphosphine complexes of formula I may be used with considerably smaller amounts of catalyst, shorter reaction times and optical yields of above 94% can be obtained.

As used throughout this application, the term "lower alkyl" means any conventional straight-chain or branched alkyl groups containing from 1 to 9 carbon atoms such as e.g. methyl, ethyl, propyl, isopropyl, n-butyl, isobutyl, tert.butyl, pentyl, hexyl, heptyl, octyl or nonyl and the like. The term "halogen" means fluorine, chlorine, bromine and iodine. Fluorine is preferred. The term "perfluoro $C_{1-20}$-alkyl" as used herein means straight or branched chains, which, however, need not have all the hydrogens replaced by fluorine; typical examples are perfluoro alkyls containing terminal $F_2HC$-groups. Branched chains may be optically active. When X is fixed to a carrier, this may be effected using any conventional linking group, an example of such a group is —COA. The term "aryl" used herein designates mononuclear aromatic hydrocarbon groups such as tolyl or phenyl which may be unsubstituted or substituted in the para- and/or meta-position the substituted groups being selected from groups such as lower alkyl, lower alkoxy, preferably methyl or methoxy groups, di-lower alkylamino groups, preferably dimethylamino groups, or carboxy, carbamoyl, cyano or lower alkoxycarbonyl group. Moreover, two aryl groups on the same phosphorus atom can be attached directly to each other via the o-position or also via a methylene, ethylene or propylene group. The term "aryloxy" designates aryloxy groups where aryl is defined as above. The term "lower alkoxy" as used herein is taken to mean a lower alkoxy group containing 1 to 9 carbon atoms such as methoxy, ethoxy, propoxy, isopropoxy, etc.

In the pictorial representation of the compounds given throughout this application, a tapered "|" notation indicates a residue situated above the plane of the molecule, while the tapered "⌇" notation indicates a residue situated below the plane of the molecule. The symbol n is 1 to 20, preferably 1 to 12 and especially 1 to 8.

The term "neutral ligand" as used throughout this specification describes a readily exchangeable ligand, which ligand can be exchanged in the hydrogenation. Exemplary neutral ligands are an olefin, e.g. ethylene, propylene, cyclooctene, 1,5-hexadiene, norbornadiene. 1,5-cyclooctadiene and the like, a nitrile such as acetonitrile or benzonitrile and also the solvent which is used, etc. When more than one neutral ligand is present, ligands differing from one another may be used.

The chiral diphosphine ligands may be conventionally recognized diphosphine ligands used in asymmetric hydrogenations and which may be fixed to a carrier. Such ligands are known and are readily accessible to a person skilled in the art. Of the conventional ligands, the chiral diphosphine ligands which may be used in the present invention are described by: Marko, L. et al., Aspects of Homogenous Catalysis, 4, 145-202 (1981); Japanese Patent Application No. 67411 of 4.6.1978 (Derwent 8180 C); German Offenlegungsschrift No. 2 161 200; European Patent Publication No. 104375. Preferred ligands are e.g. the chiral phosphines of the general formula

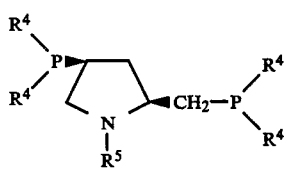

wherein $R^4$ is aryl and $R^5$ is —CO—$R^6$, —SO$_2$—$R^6$, —PO($R^6$)$_2$ or —PS($R^6$)$_2$ in which $R^6$ is aryl, lower aryl, di-arylamino, di-lower alkylamino, aryloxy or lower alkoxy.

In a preferred embodiment, the rhodium-diphosphine complexes of formula I are those in which Z is

and any two of the substituents $R^1$, $R^2$ or $R^3$ is fluorine and the third is halogen other than fluorine or perfluoro-$C_{1-20}$-alkyl. In another preferred embodiment, the diphosphine ligands of formula II are those in which $R^4$ is phenyl, p-tolyl, m-tolyl or 3,5-xylyl and $R^6$ in the residue $R^5$ is phenyl, p-tolyl, m-tolyl, p-lower alkoxycarbonylphenyl or tert.butoxy. Especially preferred phosphines are, moreover, those in which the residue $R^5$ is the group —PO($R^6$)$_2$.

The following can be named as examples of preferred diphosphine ligands:

(2S,4S)-4-(Di-m-tolylphosphino)-2-[(di-m-tolylphosphino)methyl]-1-(diphenylphosphinoyl)-pyrrolidine; (mCH$_3$—POPPM)

(2S,4S)-4-(diphenylphosphino)-2-[(diphenylphosphino)-methyl]-1-(diphenylphosphinoyl)-pyrrolidine; (POPPM)

(2S,4S)-4-(di-p-tolylphosphino)-2-[(di-p-tolylphosphino)methyl]-1-(diphenylphosphinoyl)-pyrrolidine; (pCH$_3$—POPPM)

(2S,4S)-4-(diphenylphosphino)-2-[(diphenylphosphino)-methyl]-1-(di-p-carbomethoxyphenylphosphinoyl)-pyrrolidine;

(2S,4S)-4-(diphenylphosphino)-2-[(diphenylphosphino)-methyl]-1-(tert.butoxycarbonyl)-pyrrolidine; (BPPM)

(2S,4S)-4-(di-m-tolylphosphino)-2-[(di-m-tolylphosphino)methyl]-1-(tert.butoxycarbonyl)-pyrrolidine; (mCH$_3$—BPPM).

Especially preferred rhodium-diphosphine complexes of formula I are those in which $R^1$, $R^2$ or $R^3$ is perfluoro-$C_{1-20}$-alkyl. In another especially preferred embodiment, the rhodium-diphosphine complexes of formula I are those in which Z is —CF$_3$ or Cl—CF$_2$— and the diphosphine ligand is BPPM; mCH$_3$—BPPM, POPPM or mCH$_3$—POPPM. The complexes of the formula

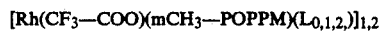

[Rh(CF$_3$—COO)(mCH$_3$—POPPM)(L$_{0,1,2,}$)]$_{1,2}$

[Rh(C$_2$F$_5$—COO)(mCH$_3$—POPPM)(L$_{0,1,2,}$)]

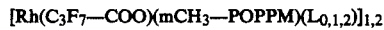

[Rh(C$_3$F$_7$—COO)(mCH$_3$—POPPM)(L$_{0,1,2}$)]$_{1,2}$ are particularly preferred.

The rhodium-diphosphine complexes of formula I can be made in a conventional manner known to one of ordinary skill. They can be manufactured, for example, by:

(a) reacting a rhodium complex of the formula

[Rh(X)(L$_m$)]$_{1,2}$     III wherein X and L are as above and m is a number 1 to 4, with a chiral diphosphine ligand; or (b) reacting a rhodium complex of the formula

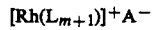

[Rh(L$_{m+1}$)]$^+$A$^-$     IV wherein L and m are as above and A$^-$ is an anion, especially BF$_4^-$, ClO$_4^-$, PF$_6^-$ or B(C$_6$H$_5$)$_4^-$, with a chiral diphosphine ligand and a salt containing the anion X; or (c) reacting a rhodium-diphosphine complex of the formula

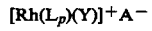

[Rh(L$_p$)(Y)]$^+$A$^-$     V wherein L, Y and A$^-$ are as above and p is 1 to 3, with a salt containing the anion X; or (d) reacting a chiral rhodium-diphosphine complex of the formula

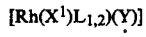

[Rh(X$^1$)L$_{1,2}$)(Y)]     VI wherein X$^1$ is halogen and L and Y are as above, with a silver salt or thallium salt of the formula

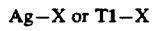

Ag—X or Tl—X     VII wherein X is as above.

The reactions of the rhodium complexes of formulae III, IV, V and VI in accordance with reaction variants (a)–(d) can be carried out in a manner known in the art. These reactions are conveniently carried out in an inert organic solvent. Examples of such solvents are aromatic hydrocarbons such as benzene, toluene etc, esters such as ethyl acetate etc, cyclic ethers such as tetrahydrofuran or dioxan, lower alcohols such as methanol, ethanol and the like or also mixtures thereof. The reaction can be carried out at temperatures in the range of about 0° C. to about 100° C., preferably at about 15° C. to about 60° C. In carrying out this reaction oxygen must be excluded.

The term "salt containing the anion X" as used herein includes ammonium salts, alkali metal salts, alkaline earth metal salts as well as other suitable metal salts. Such salts are known substances. In order to increase the solubility of such salts in certain solvents, a suitable ether, e.g. a crown ether, can be added if desired.

The rhodium-diphosphine complexes of formula I are catalysts or precursors thereof. Since their true chemical structure can not be given with certainty, they are also characterized in that they are obtainable by reacting a rhodium complex of formulae III–VI in accordance with reactions (a) to (d) mentioned previously.

The rhodium complexes of formulae III, IV, V and VI which are used as starting materials are known substances or analogues of known substances which can be prepared readily in analogy to the known substances.

As already mentioned, the rhodium-diphosphine complexes of formula I in accordance with the invention serve as catalysts in asymmetric hydrogenations. They are of particular interest in connection with the asymmetric hydrogenation of α,β-unsaturated acids and esters as well as of α-keto-carboxylic acids and esters and of α-keto-lactones. In particular, they are of interest for the asymmetric hydrogenation of dihydro-4,4-dimethyl-2,3-furandione (ketopantolactone) to the corresponding R-(α-hydroxy-β,β-dimethyl-γ-butyrolactone) [R-(—)-pantolactone].

In order to carry out the aforementioned asymmetric hydrogenation, the complexes of formula I can be added as such to a solution of an asymmetric compound to be hydrogenated. According to another embodiment of this invention the complexes of formula I can also be formed in situ in the presence of an asymmetric compound to be hydrogenated.

The asymmetric hydrogenation can be carried out in suitable organic solvents which are inert under the reaction conditions. Examples of such organic solvents are lower alkanols such as e.g. methanol or ethanol, aromatic hydrocarbons such as benzene or toluene, cyclic ethers such as tetrahydrofuran or dioxan, esters such as e.g. ethyl acetate and mixtures thereof and the like. The ratio between rhodium and the ligand Y conveniently lies in the range of about 0.5 and about 5 mol, preferably between about 0.5 and about 2 mol, of rhodium per mol of ligand. The ratio between rhodium and the residue X conveniently lies in the range of about 0.01 and about 20, preferably between about 0.5 and about 10 mol, of rhodium per mol of residue X. The ratio between rhodium, in the complexes of formula I, and the compounds to be hydrogenated conveniently lies in the range of about 0.00001 and about 5 wt.%, preferably between about 0.0001 and about 0.01 wt.%.

The asymmetric hydrogenations using the complexes of formula I can be carried out conveniently at temperatures in the range of about 0° C. to about 100° C., preferably of about 20° C. to about 70° C. These hydrogenations are conveniently carried out under pressure, especially under a pressure in the range of about 1 to 100 bar, preferably 2 to 50 bar.

The following Examples serve to illustrate the invention and are in no way a limitation.

In these Examples the abbreviations used have the following significance:
COD=1,5-cyclooctadiene
BPPM; mCH$_3$—BPPM; POPPM; mCH$_3$—POPPM: diphosphines mentioned on page 5.

The optical rotations of (R)-(−)-pantolactone at 589 nm (D-line) were measured at 20° C. and at a concentration of 3% in ion-free water.

The values for the optical purities are based on $[\alpha]_D^{20} = -51.6°$ (c=3, H$_2$O) for purest (R)-(−)-pantolactone.

EXAMPLE 1

90.5 mg (0.125 mmol) of 98% (2S,4S)-4-(di-m-tolylphosphino)-2-[(di-m-tolylphosphino)methyl]-1-(diphenylphosphinoyl)pyrrolidine (=mCH$_3$—POPPM), 50.2 mg (0.124 mmol) of bis(1,5- cyclooctadiene)rhodium(I) tetrafluoroborate and 44.4 mg (0.125 mmol) of tetrabutyl-ammonium trifluoroacetate were added in a glove box (O$_2$-content less than 1 ppm) to a 100 ml measuring flask. The flask was then made up to the 100 ml mark with about 100 ml of O$_2$-free toluene. The suspension obtained was subsequently stirred at 22° C. for 24 hours, whereby an orange turbid solution formed.

EXAMPLE 2

200 g (1.561 mol) of dihydro-4,4-dimethyl-2,3-furandione (ketopantolactone) and 600 ml of toluene were placed in a 1 liter stirring autoclave. After heating to 40° C. the air was removed from the autoclave by evacuation 5 times with a high vacuum pump (0.05–0.1 bar) and gasification with 10 bar of hydrogen each time. The temperature of the ketopantolactone solution was then adjusted to 35° C., the pressure was lowered to 0.5 bar and immediately 50 ml of the catalyst solution prepared in accordance with Example 1 were sucked in with the complete absence of O$_2$. After pressurizing to 40 bar of hydrogen the mixture was hydrogented while stirring and at constant pressure (40 bar) at 35° C. for 1 hour and at 45° C. for 4 hours. After a total hydrogenation time of 5 hours the pale yellow hydrogenation solution was removed under pressure from the autoclave and the autoclave was subsequently rinsed 3 times with 100 ml of toluene each time. The combined toluene solutions were evaporated on a rotary evaporator at 60° C./17 mbar. The residue (210 g) was distilled at 130°–150° C. bath temperature and 12 mbar. There were obtained 201.6 g (99.3%) of R-($\alpha$-hydroxy-$\beta,\beta$-dimethyl-$\gamma$-butyrolactone (=R-(−)-pantolactone) with an optical purity of 90.7%. $[\alpha]_D^{20} = -46.8°$ (c=3 in H$_2$O).

EXAMPLE 3

In a manner analogous to Example 1, a catalyst solution (100 ml) was prepared from 29.0 mg (0.0625 mmol) of chloronorbornadiene-rhodium(I) dimer, 70.0 mg (0.126 mmol) of (2S,4S)-4-(diphenylphosphino)-2-[(diphenylphosphino)methyl]-1-(tert.butoxycarbonyl)-pyrrolidine (BPPM) and 27.8 mg (0.0126 mmol) of silver trifluoroacetate.

EXAMPLE 4

A 500 ml autoclave was loaded in a glove box with 40 g (0.31 mol) of ketopantolactone, 200 ml of toluene and 10 ml of catalyst solution (in accordance with Example 3). The hydrogenation was carried out at 30° C., a constant pressure of 40 bar of H$_2$ and with intensive stirring. The temperature of the solution rose to 43° C. After 1 hour the conversion amounted to 98%. After a total of 3 hours the mixture was worked-up analogously to Example 2, pure (R)-pantolactone being obtained. $[\alpha]_D^{20} = -46.0°$. Optical purity 89.1%.

EXAMPLE 5

In a manner analogous to Example 1, a catalyst solution (100 ml) was prepared from 23.8 mg (0.0625 mmol) of bis(acetonitrile)-1,5-cyclooctadiene-rhodium tetrafluroroborate, 75.3 mg (0.0625 mmol) of (2S,4S)-4-(di-m-tolylphosphino)-2-[(di-m-tolylphosphino)methyl]-1-(diphenylphosphinoyl)-pyrrolidine(mCH$_3$—POPPM) and 22.2 mg (0.0625 mmol) of tetrabutylammonium trifluoroacetate.

EXAMPLE 6

The hydrogenation of 40.0 g of ketopantolactone with 10 ml of catalyst solution prepared according to Example 5 was carried out as described in Example 4. After a hydrogenation time of 2 hours the mixture was worked-up analogously to Example 2, pure (R)-pantolactone being obtained. $[\alpha]_D^{20} = -46.7°$. Optical purity 90.5%.

EXAMPLE 7

In a manner analogous to Example 1, a catalyst solution (100 ml) was prepared from 29.0 mg (0.0625 mmol) of bis(1,5-cyclooctadiene)rhodium hexafluorophosphate, 45.3 mg (0.0625 mmol) of mCH$_3$—POPPM and 25.3 mg (0.0625 mmol) of tetrabutylammonium perfluoropropionate.

EXAMPLE 8

The hydrogenation of 40 g of ketopantolactone with 10 ml of catalyst solution prepared in accordance with Example 7 was carried out as described in Example 4. After a reaction time of 3 hours the mixture was worked-up analogously to Example 2. There was obtained pure (R)-pantolactone, $[\alpha]_D^{20} = -48.3°$. Optical purity 93.6%.

EXAMPLE 9

In a manner analogous to Example 1, a catalyst solution (100 ml) was prepared from 29.0 mg (0.0625 mmol) of bis(1,5-cyclooctadiene)rhodium hexafluorophosphate, 45.3 mg (0.0625 mmol) of mCH$_3$—POPPM and 28.5 mg (0.0625 mmol) of tetrabutylammonium perfluorobutyrate.

EXAMPLE 10

The hydrogenation of 40.0 g of ketopantolactone with 10 ml of catalyst solution prepared according to Example 9 was carried out as described in Example 4. After a hydrogenation time of 3 hours the mixture was worked-up analogously to Example 2, pure (R)-pantolactone being obtained. $[\alpha]_D^{20} = -48.4°$. Optical purity 93.8%.

EXAMPLE 11

In a manner analogous to Example 1, a catalyst solution (100 ml) was prepared from 29.0 mg (0.0625 mmol) of [Rh(COD)$_2$]PF$_6$, 45.3 mg (0.0625 mmol) of mCH$_3$—POPPM and 23.0 mg (0.0625 mmol) of tetrabutylammonium chlorodifluoroacetate.

EXAMPLE 12

The hydrogenation of 40.0 g of ketopantolactone with 10 ml of catalyst solution prepared according to Example 11 was carried out as described in Example 4. After a hydrogenation time of 2 hours the mixture was worked-up analogously to Example 2, pure (R)-pantolactone being obtained. $[\alpha]_D^{20} = -46.9°$. Optical purity 91.0%.

EXAMPLE 13

In a manner analogous to Example 1, a catalyst solution (100 ml) was prepared from 58.0 mg (0.0125 mmol) of [Rh(COD)$_2$]PF$_6$, 90 mg (0.125 mmol) of mCH$_3$—POPPM and 44.0 mg (0.125 mmol) of tetrabutylammonium trifluoroacetate.

EXAMPLE 14

The hydrogenation of 40 g of ketopantolactone with 10 ml of catalyst solution prepared according to Example 13 was carried out analogously to Example 4, but at a pressure of 5 bar of H$_2$. After a hydrogenation time of 10 hours the mixture was worked-up analogously to Example 2. Pure (R)-pantolactone was obtained. $[\alpha]_D^{20} = -47.7°$. Optical purity 92.2%.

EXAMPLE 15

A solution of the catalyst in ethyl acetate was prepared in an analogous manner to Example 13.

EXAMPLE 16

The hydrogenation of 40 g of ketopantolactone with 10 ml of catalyst solution prepared according to Example 15 at 30° C./40 bar of H$_2$ for 20 hours and working-up in accordance with Example 2 gave 97.5% (R)-pantolactone. $[\alpha]_D^{20} = -46.8°$. Optical purity 90.7%.

EXAMPLE 17

A 500 ml steel autoclave was loaded in a glove box (O$_2$-content less than 1 ppm) with 40.0 g (0.31 mol) of ketopantolactone, 210 ml of toluene, 180.6 mg (0.389 mmol) of [Rh(COD)$_2$]PF$_6$, 237.3 mg (0.389 mmol) of mCH$_3$—BPPM and 138.3 mg (0.389 mmol) of tetrabutylammonium trifluoroacetate. The hydrogenation was carried out at a constant pressure of 40 bar of H$_2$ at 30° C. and with intensive stirring. By virtue of the exothermic reaction the temperature rose to 55° C. A conversion of above 99% was achieved after 1.2 hours. After a total hydrogenation time of 2 hours the mixture was worked-up as described in Example 2. Pure (R)-pantolactone was obtained. $[\alpha]_D^{20} = -46.0°$. Optical purity 89.1%.

EXAMPLE 18

A 500 ml steel autoclave was loaded in a glove box (O$_2$-content less than 1 ppm) with 40.0 g (0.31 mol) of ketopantolactone, 210 ml of toluene, 180.6 mg (0.389 mmol) of [Rh(COD)$_2$]PF$_6$, 254.3 mg (0.389 mmol) of POPPM and 138.3 mg (0.389 mmol) of tetrabutylammonium trifluoroacetate. The hydrogenation was carried out at a constant pressure of 40 bar of H$_2$, at 30° C. and with intensive stirring. By virtue of the exothermic reaction the temperature rose to 58° C. A conversion of above 99% was achieved after 1 hour. After a total hydrogenation time of 2 hours the mixture was worked-up as described in Example 2. Pure (R)-pantolactone was obtained. $[\alpha]_D^{20} = -46.6°$. Optical purity 90.4%.

EXAMPLE 19

In a manner analogous to Example 18, the hydrogenation was carried out using 180.6 mg (0.389 mmol) of [Rh(COD)$_2$]PF$_6$ and 299.4 mg (0.389 mmol) of (2S,4S)-4-(diphenylphosphino)-2-[(diphenylphosphino)methyl]-1-(di-p-carbomethoxyphenylphosphinoyl)-pyrrolidine in place of POPPM. After a reaction time of 2 hours the mixture was worked-up analogously to Example 2, pure (R)-pantolactone being obtained. $[\alpha]_D^{20} = -46.2°$. Optical purity 89.6%.

EXAMPLE 20

In a manner analogous to Example 18, the hydrogenation was carried out using 336.2 mg (0.389 mmol) of [Rh(COD)(BPPM)]ClO$_4$ and 138.3 mg (0.389 mmol) of tetrabutylammonium trifluoroacetate. After a reaction time of 2 hours the mixture was worked-up analogously to Example 2, pure (R)-pantolactone being obtained. $[\alpha]_D^{20} = -47.5°$. Optical purity 92.0%.

EXAMPLE 21

In a manner analogous to Example 18, the hydrogenation of 40 g of ketopantolactone was carried out using 241.1 mg (0.389 mmol) of (2S,4S)-4-(diphenylphosphino)-2-[(diphenylphosphino)methyl]-1-(10-undecenoyl)-pyrrolidine, 144.7 mg (0.389 mmol) of tetrabutylammonium chlorodifluoroacetate and 180.6 mg (0.389 mmol) of [Rh(COD)$_2$]PF$_6$. After a reaction time of 1.5 hours the mixture was worked-up analogously to Example 2, pure (R)-pantolactone being obtained. $[\alpha]_D^{20} = -46.0°$. Optical purity 89.2%.

EXAMPLE 22

A 500 ml steel autoclave was loaded in a glove box (O$_2$-content less than 1 ppm) with 2.6 g (20 mmol) of itaconic acid, 150 ml of toluene, 50 ml of methanol, 2.02 g (20 mmol) of triethylamine, 36.0 mg (0.0886 mmol) of [Rh(COD)$_2$]BF$_4$, 49 mg (0.0886 mmol) of BPPM and 31.5 mg (0.0886 mmol) of tetrabutylammonium trifluoroacetate. the hydrogenation was carried out at a constant pressure of 6 bar of H$_2$, at 30° C. and with intensive stirring. After a total hydrogenation time of 3 hours the reaction solution was evaporated and the residue was dissolved in 40 ml of 2N sodium hydroxide solution.

The aqueous phase was washed with toluene, adjusted to pH 2 with conc. hydrochloric acid, saturated with NaCl and extracted with 3×100 ml of ether. The combined ether phases were dried over $Na_2SO_4$ and evaporated. There were obtained 2.4 g (92.3%) of methylsuccinic acid as white crystals. M.p. 111°–112° C. $[\alpha]_D^{20} = -16.2°$ (c=5, EtOH). Optical purity 95.4%.

EXAMPLE 23

An autoclave was loaded in a glove box with 5.87 g (20 mmol) of trans-α-acetamido-4-acetoxy-3-methoxycinnamic acid, 200 ml of ethanol, 60.7 mg (0.6 mmol) of triethylamine, 81.2 mg (0.20 mmol) of $[Rh(COD)_2]BF_4$, 121.8 mg (0.22 mmol) of BPPM and 71.1 mg (0.20 mmol) of tetrabutylammonium trifluoroacetate. The hydrogenation was carried out at 30° C. and 50 bar of $H_2$ for 3 hours. The reaction solution was evaporated and the residue (5.6 g) was dissolved in 40 ml of 4.5% aqueous $NaHCO_3$ solution. The aqueous phase was washed with toluene, adjusted to pH 3 with conc. HCl, saturated with NaCl and extracted with chloroform. The organic phase was dried over $Na_2SO_4$ and evaporated. There were obtained 4.85 g (83%) of 3-(4-acetoxy-3-methoxyphenyl)-N-acetyl-D-alanine as pale yellow crystals. M.p. 174°–175° C. $[\alpha]_D^{20} = -36.7°$ (c=1, $CH_3OH$). Optical purity 90.6%.

EXAMPLE 24

A 500 ml steel autoclave was loaded in a glove box ($O_2$-content less than 1 ppm) with 40.0 g (0.31 mol) of ketopantolactone, 205 ml of tetrahydrofuran, 180.6 mg (0.389 mmol) of $[Rh(COD)_2]PF_6$, 215.2 mg (0.389 mmol) of BPPM and 138.3 mg of tetrabutylammonium trifluoroacetate. The hydrogenation was carried out analogously to Example 18. After a reaction time of 1 hour the mixture was worked-up analogously to Example 2, pure (R)-pantolactone being obtained. $[\alpha]_D^{20} = -47.8°$. Optical purity 92.7%.

EXAMPLE 25

In a manner analogous to Example 1, a catalyst solution (100 ml) was prepared from 29 mg (0.0625 mmol) of $[Rh(COD)_2]PF_6$, 45.3 mg (0.0625 mmol) of mCH$_3$—POPPM and 41.4 mg (0.0625 mmol) of tetrabutylammonium perfluorocaprylate.

EXAMPLE 26

The hydrogenation of 40.0 g (0.31 mol) of ketopantolactone with 10 ml of catalyst solution prepared according to Example 25 was carried out as described in Example 4. After a hydrogenation time of 3 hours the mixture was worked-up analogously to Example 2, pure (R)-pantolactone being obtained. $[\alpha]_D^{20} = -48.3°$. Optical purity 93.6%.

EXAMPLE 27

A 500 ml steel autoclave was loaded in a glove box ($O_2$-content less than 1 ppm) with 40.0 g (0.31 mol) of ketopantolactone, 210 ml of toluene, 180.6 mg (0.389 mmol) of $[Rh(COD)_2]PF_6$, 215.2 mg (0.389 mmol) of BPPM and 176.4 mg (0.389 mmol) of tetrabutylammonium pentafluorobenzoate. The hydrogenation was carried out at a constant pressure of 40 bar of $H_2$, at 30° C. and with intensive stirring. By virtue of the exothermic reaction the temperature rose to 40° C. After a hydrogenation time of 3 hours the mixture was worked-up as described in Example 2. Pure (R)-pantolactone was obtained. $[\alpha]_D^{20} = -45.8°$. Optical purity 88.8%.

EXAMPLE 28

40.1 mg (0.062 mmol) of a 40% aqueous tetrabutylammonium hydroxide solution, 22.0 mg (0.062 mmol) of perfluoroheptanoic acid, 25.1 mg (0.062 mmol) of bis(1,5-cyclooctadiene)rhodium(I) tetrafluoroborate and 44.7 mg (0.062 mmol) of mCH$_3$—POPPM were added in a glove box ($O_2$-content less than 1 ppm) to a 100 ml measuring flask. The flask was then made up to the 100 ml mark with about 100 ml of $O_2$-free toluene. The suspension obtained was subsequently stirred at 22° C. for 24 hours, whereby an orange, almost clear solution formed.

EXAMPLE 29

A 500 ml autoclave was loaded in a glove box with 40 g (0.31 mol) of ketopantolactone, 200 ml of toluene and 10 ml of catalyst solution prepared according to Example 28. The hydrogenation was carried out at 40° C., a constant pressure of 40 bar of $H_2$ and with intensive stirring. After 1 hour the conversion amounted to 99.9%. After a total of 2.5 hours the mixture was worked-up analogously to Example 2, pure (R)-pantolactone being obtained. $[\alpha]_D^{20} = -47.5°$. Optical purity 92.0%.

EXAMPLE 30

In a manner analogous to Example 28, a catalyst solution (100 ml) was prepared from 40.1 mg (0.062 mmol) of a 40% aqueous tetrabutylammonium hydroxide solution, 29.0 mg (0.062 mmol) of perfluorononanoic acid, 25.1 mg (0.062 mmol) of bis(1,5-cyclooctadiene)rhodium(I) tetrafluoroborate and 44.7 mg (0.062 mmol) of mCH$_3$—POPPM.

EXAMPLE 31

The hydrogenation of 40.0 g of ketopantolactone with 10 ml of catalyst solution prepared according to Example 30 was carried out as described in Example 29. After a hydrogenation time of 2.5 hours the mixture was worked-up analogously to Example 2, pure (R)-pantolactone being obtained. $[\alpha]_D^{20} = -47.5°$. Optical purity 92.0%.

EXAMPLE 32

In a manner analogous to Example 28, a catalyst solution (100 ml) was prepared from 40.1 mg (0.062 mmol) of a 40% aqueous tetrabutylammonium hydroxide solution, 31.8 mg (0.062 mmol) of perfluorodecanoic acid, 25.1 mg (0.062 mmol) of bis(1,5-cyclooctadiene)rhodium(I) tetrafluoroborate and 44.7 mg (0.062 mmol) of mCH$_3$—POPPM.

EXAMPLE 33

The hydrogenation of 40.0 g of ketopantolactone with 10 ml of catalyst solution prepared according to Example 32 was carried out as described in Example 29. After a hydrogenation time of 2.5 hours the mixture was worked-up analogously to Example 2, pure (R)-pantolactone being obtained. $[\alpha]_D^{20} = -47.8°$. Optical purity 92.7%.

EXAMPLE 34

In a manner analogous to Example 28, a catalyst solution (50 ml) was prepared from 127.1 mg (0.195 mmol) of a 40% aqueous tetrabutylammonium hydroxide solution, 32.3 mg (0.195 mmol) of α-fluorocinnamic acid, 78.5 mg (0.195 mmol) of bis(1,5-cyclooctadiene)r- hodium(I) tetrafluoroborate and 140.9 mg (0.0195 mmol) of mCH$_3$—POPPM.

EXAMPLE 35

The hydrogenation of 20.0 g of ketopantolactone, dissolved in 55 ml of toluene, with 50 ml of catalyst solution prepared according to Example 34 was carried out as described in Example 29. After a hydrogenation time of 1 hour the mixture was worked-up analogously to Example 2, pure (R)-pantolactone being obtained. $[\alpha]_D^{20} = -46.4°$. Optical purity 89.9%.

EXAMPLE 36

In a manner analogous to Example 28, a catalyst solution (100 ml) was prepared from 254.2 mg (0.389 mmol) of a 40% aqueous tetrabutylammonium hydroxide solution, 65.4 mg (0.389 mmol) of 2-fluoro-3-phenyl-propanoic acid, 157.8 mg (0.389 mmol) of bis(1,5-cyclooctadiene)rhodium(I) tetrafluoroborate and 281.0 mg (0.389 mmol) of mCH$_3$—POPPM.

EXAMPLE 37

The hydrogenation of 40.0 g of ketopantolactone, dissolved in 110 ml of toluene, with 100 ml of catalyst solution prepared according to Example 36 was carried out as described in Example 29. After a hydrogenation time of 2 hours the mixture was worked-up analogously to Example 2. pure (R)-pantolactone being obtained. $[\alpha]_D^{20} = -47.9°$. Optical purity 92.8%.

EXAMPLE 38

A 500 ml steel autoclave was loaded in a glove box (O$_2$-content less than 1 ppm) with 10.2 g (0.1 mol) of methyl pyruvate, 200 ml of benzene, 32.1 mg (0.0496 mmol) of di-μ-trifluoroacetate-bis(1,5-cyclooctadiene)-di-rhodium and 56.0 mg (0.0991 mmol) of BPPM. The hydrogenation was carried out at a constant pressure of 20 bar of H$_2$, at 21° C. and with intensive stirring. The conversion after 4 hours amounted to 98.4%. The reaction solution was evaporated and the residue was distilled at atmospheric pressure. There was obtained methyl (R)-(+)-lactate (b.p. 143°-145°). In order to determine the enantiomer excess in a gas chromatogram, a sample thereof was converted quantitatively into the camphanic acid ester. Enantiomer excess: 80.1%.

EXAMPLE 39

As a comparison, the hydrogenation of 10.2 g of methyl pyruvate was carried out in a manner analogous to Example 38 using 24.5 mg (0.0496 mmol) of [Rh(COD)Cl]$_2$ in place of the rhodium trifluoroacetate complex. There was obtained methyl R-(+)-lactate (b.p. 143°-145°). Enantiomer excess: 70.6%. For this hydrogenation under identical conditions an optical yield of 66.3% is given in the literature (I. Ojima, T. Kogure and K. Achiwa, J. Chem. Soc., Chem. Commun; 1977, 428).

EXAMPLE 40

The hydrogenation of 11.6 g (0.1 mol) of ethyl pyruvate was carried out in a manner analogous to Example 38. The conversion was 99.2% after 23 hours. There was obtained ethyl (R)-(+)-lactate (b.p. 152°-154°). Enantiometer excess: 79.5%.

EXAMPLE 41

The hydrogenation of 11.6 g of ethyl pyruvate was carried out in a manner analogous to Example 39. There was obtained ethyl (R)-(+)-lactate (b.p. 151°-154°). Enantiomer excess: 71.2%. For the hydrogenation under identical conditions an optical yield of 65.3% is given in the literature (K. Achiwa, Tetrahedron Lett. 1977, 3735).

EXAMPLE 42

57.6 mg of a copolymer (phosphorus content 1.33%), prepared from (2S,4S)-4-(diphenylphosphino)-2-[(diphenylphosphino)methyl]-1-(4-pentenoyl)-pyrrolidine and 2-hydroxyethyl methacrylate were added in a glove box (O$_2$-content less than 1 ppm) to a solution of 4.02 mg (0.0062 mmol) of [Rh(COD)CF$_3$COO]$_2$ in 20 ml of toluene and the suspension obtained was stirred at 22° C. for 24 hours.

EXAMPLE 43

The hydrogenation of 20.0 g of ketopantolactone with the catalyst suspension prepared according to Example 42 was carried out as described in Example 29, but at 60° C. After a hydrogenation time of 24 hours the mixture was worked-up analogously to Example 2, pure (R)-pantolactone being obtained. $[\alpha]_D^{20} = -43.6°$. Optical purity 84.4%.

What is claimed is:

1. A chiral rhodium-diphosphine complex of the formula $$[Rh(X)(Y)(L)_m]_{1 \text{ or } 2}$$

wherein X, which may be fixed to a carrier, is $$-O-\overset{O}{\underset{}{C}}-\overset{R^1}{\underset{R^3}{\overset{|}{C}}}-R^2 \text{ or } -O-\overset{O}{\underset{}{C}}-\overset{R^3}{\underset{}{C}}=C\overset{R_1}{\underset{R^2}{\diagdown}};$$

$R^1$, $R^2$ and $R^3$ independently equal halogen, lower alkyl, perfluorophenyl, perfluoro-C$_{1-20}$-alkyl, hydrogen, —COA or AOC—(CF$_2$)$_n$—; A is —OR or —NR'$_2$; R is hydrogen, lower alkyl or a cation; R' is hydrogen or lower alkyl; n is 1 to 20; m is 1 to 4; provided that at least one of $R^1$, $R^2$ and $R^3$ must equal fluorine; Y is a chiral diphosphine ligand of the formula $$\begin{array}{c} R^4 \diagdown \\ R^4 \diagup P \diagdown \\ \diagdown \diagup \diagdown CH_2-P \diagup R^4 \\ N \diagdown R^4 \\ | \\ R^5 \end{array} \quad \text{II}$$

$R^4$ is aryl; $R^5$ is —CO—$R^6$, —SO$_2$—$R^6$, —PO($R^6$)$_2$ or —PS($R^6$)$_2$; $R^6$ is aryl, lower alkyl, di-arylamino, di-lower alkylamino, aryloxy or lower alkoxy; and L is a neutral ligand which can be exchanged during a halogenation reaction.

2. The chiral complex of claim 1, wherein at least two of the substituents $R^1$, $R^2$ and $R^3$ represent fluorine.

3. The chiral complex of claim 1, wherein X is CF$_3$—COO$^-$ or perfluoro-C$_{1-20}$-alkyl.

4. The chiral complex of claim 1, wherein $R^5$ is —PO($R^6$)$_2$.

5. The chiral complex of claim 1, wherein $R^4$ is m-tolyl and $R^6$ is phenyl.

6. The chiral complex of claim 1, wherein L is a neutral ligand selected from the group consisting of 1,5-cyclooctadiene, norbornadiene, ethylene, propylene, cyclooctene, acetonitrile or benzonitrile.

7. A chiral complex according to claim 1, wherein X is

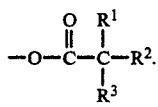

8. A chiral complex according to claim 1, wherein X is

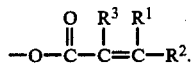

9. A chiral complex according to claim 1, wherein at least two of $R^1$, $R^2$ and $R^3$ are equal to fluorine.

10. A chiral complex according to claim 9, wherein X is

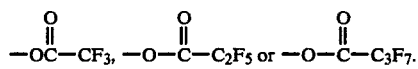

11. A chiral complex according to claim 9 wherein $R^1$ and $R^2$ are fluorine and $R^3$ is perfluoro-$C_{1-20}$-alkyl.

12. A chiral complex according to claim 9, wherein $R^5$ is $-PO(R^6)_2$.

13. A chiral complex according to claim 12, wherein $R^4$ is m-tolyl and $R^6$ is phenyl.

14. A chiral complex of according to claim 13, wherein L is 1,5-cyclooctadiene or cyclooctene.

15. A chiral complex according to claim 1 wherein the ratio of rhodium to Y in said chiral rhodium-diphosphine complex is from about 0.05–5 mol of rhodium per 1 mol of Y; and the ratio of rhodium to X in said chiral rhodium-diphosphine complex is from about 0.01 to 20 mol of rhodium per 1 mol of X.

16. A chiral complex according to claim 15 wherein the ratio of rhodium to Y is from about 0.05–2.0 mol of rhodium per 1 mol of Y and wherein the ratio of rhodium to X is from about 0.01–10 mol of rhodium per 1 mol X.

* * * * *

UNITED STATES PATENT AND TRADEMARK OFFICE
CERTIFICATE OF CORRECTION

PATENT NO. : 4,652,657

DATED : March 24, 1987

INVENTOR(S) : Broger, et al.

It is certified that error appears in the above-identified patent and that said Letters Patent is hereby corrected as shown below:

Claim 1, lines 61 and 62: after "during a" delete "halogenation" and insert therefor -- hydrogenation --

Signed and Sealed this

Nineteenth Day of December, 1989

Attest:

JEFFREY M. SAMUELS

Attesting Officer     Acting Commissioner of Patents and Trademarks